United States Patent [19]

Yue et al.

[11] Patent Number: 5,393,772

[45] Date of Patent: Feb. 28, 1995

[54] USE OF, AND METHOD OF TREATMENT USING, HYDROXYCARBAZOLE COMPOUNDS FOR INHIBITION OF SMOOTH MUSCLE MIGRATION AND PROLIFERATION

[75] Inventors: Tian-Li Yue, Havertown; Eliot H. Ohlstein, Glenmoore; Giora Z. Feuerstein, Wynnewood, all of Pa.

[73] Assignees: Boehringer Mannheim Pharmaceuticals Corporation; SmithKline Beecham Corporation Limited Prtnrshp No. 1, both of Rockville, Md.

[21] Appl. No.: 157,588

[22] Filed: Nov. 24, 1993

[51] Int. Cl.$^6$ .............................................. A61K 31/40
[52] U.S. Cl. ..................................... 514/410; 514/411
[58] Field of Search .............................. 514/410, 411

[56] References Cited

U.S. PATENT DOCUMENTS 5,308,862  4/1994  Ohlstein ........................... 514/411

OTHER PUBLICATIONS

Albrightson, C et al Pharmacol. Commun. (1992) 1(4) 267–272.
Ohlstein, E et al Proc. Natl. Acad. Sci U.S.A. 1993 90(13) 6189–93.
Sung, C et al, J. Cardiovasc. Pharmacology (1993) 21(2), 221–7.

Primary Examiner—Paul J. Killos
Attorney, Agent, or Firm—Yuriy P. Stercho; Stuart R. Suter; Edward T. Lentz

[57] ABSTRACT

The present invention provides a new medical use of the hydroxycarbazole compounds of Formula (I), preferably the hydroxylated metabolites of 1-(carbazol-4-yloxy-3-[[2-(o-methoxyphenoxy)ethyl]amino]-2-propanol)(carvedilol), for inhibiting the migration and proliferation of smooth muscle cells. In particular, the present invention provides a new use for the hydroxycarbazole compounds of Formula (I) for prevention of restenosis following percutaneous transluminal coronary angioplasty (PTCA), suppression of the progression of vascular hypertrophy associated with hypertension, and prevention of development of atherosclerosis.

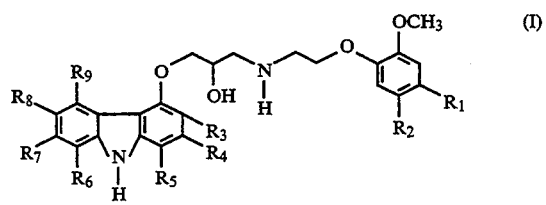

wherein:
$R_1$–$R_9$ are independently —H or —OH, with the proviso that a at least one of $R_1$–$R_9$ is OH.

32 Claims, No Drawings

USE OF, AND METHOD OF TREATMENT USING, HYDROXYCARBAZOLE COMPOUNDS FOR INHIBITION OF SMOOTH MUSCLE MIGRATION AND PROLIFERATION

FIELD OF INVENTION

The present invention relates to a new medical use of the hydroxycarbazole compounds of Formula (I), preferably the hydroxylated metabolites of 1-(carbazol-4-yloxy-3-[[2-(o-methoxyphenoxy)ethyl]amino]-2-propanol)(carvedilol), for inhibiting the migration and proliferation of smooth muscle cells. In particular, the present invention provides a new use of hydroxycarbazole compounds of Formula I for prevention of restenosis following percutaneous transluminal coronary angioplasty (PTCA), suppression of the progression of vascular hypertrophy associated with hypertension, and prevention of development of atherosclerosis.

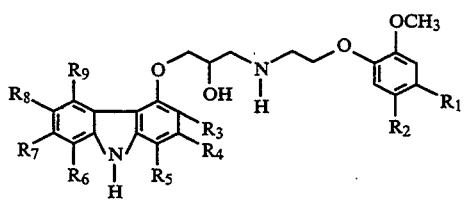

wherein:
$R_1$–$R_9$ are independently —H or —OH, with the proviso that a at least one of $R_1$–$R_9$ is OH.

BACKGROUND OF THE INVENTION

Abnormal vascular smooth muscle migration and proliferation is associated with cardiovascular disorders such as atherosclerosis, hypertension and most endovascular procedures. Abnormal vascular smooth muscle migration and proliferation is a common complication of percutaneous transluminal coronary angioplasty (PTCA). The incidence of chronic restenosis resulting from vascular smooth muscle proliferation following PTCA has been reported to be as high as 40–45% within 3–6 months. Capron, L., Huedes, D., Chajara, A. and Bruneval, P. (1991) *J. Cardiovasc. Pharmacol.*, 18, 207–211; Bourassa, M. (1992) *J. Am. Coll. Cardiol.*, 19, 1410–1411. Several neurohumoral factors, including angiotensin II and norepinephrine, as well as growth factors, including platelet-derived growth factor (PDGF) and basic fibroblast growth factor (FGF), have been implicated in the development of vascular restenosis in vivo. Bourassa, M. et al. supra; Powell, J. S., Clozel, J. P., Muller, R. K. M., Kuhn, H., Hefti, F., Hosang, M. and Baumgartner, H. R. (1989) *Science*, 245, 186–198; Clozel, J. P., Hess, P., Michael, C., Schietinger, K. and *Hypertension*, 18(Suppl. II), 1155–1159; Fingerle, J., Sanders, K. H. and Fotev, Z. (1991) *Basic Res. Cardiol.*, 86, 75–81; Fomey-Prescott, M., Webb, R. L. and Reidy, M.A. (1991) *Am. J. Pathol.*, 139, 1291–1296; Kauffman, R. F., Bean, J. S., Zimmerman, K. M., Brown, R. F. and Steinberg, M. I. (1991) *Life Sci.*, 49, 223–228; Azuma, H. Y. and Hamasaki, H. (1992) *Br. J. Pharmacol.*, 106, 665–671; Ferns, G. A. A., Raines, E. W., Sprugel, K. H., Motani, A. S., Reidy, M. A. and Ross, R. (1991) *Science*, 253, 1129–1132; and Lindner, V. and Reidy, M. A. (1991) *Proc. Natl. Acad. Sci.* (USA), 88, 3739–3743.

The high incidence of vascular reocclusion associated with PTCA has led to the development of in vivo animal models of restenosis and the search for agents to prevent restenosis. Angiotensin II receptor antagonists, angiotensin converting enzyme (ACE) inhibitors, α-adrenoreceptor antagonists and growth factor antibodies have generally produced only a modest (10–50%) reduction of vascular restenosis in such animal models. Powell, J. S., et al., supra; Fingerle, J. et al., supra; Forney-Prescott, M. et al., supra; and Kauffman, R. F., et al., supra. Clinical studies with ACE inhibitors (which showed only a moderate protective effect in animal models of restenosis) have failed to demonstrate a significant efficacy in the prevention of angiographically-defined restenosis in humans. Popma, J. J., Califf, R. M. and Topol, E. J. (1991) *Circulation*, 84, 426–1436. This limited or insignificant protection against vascular restenosis affected by agents with specific mechanisms of action most likely reflects the complex nature of the pathophysiology underlying vascular restenosis. A multiplicity of chemotactic and mitogenic factors are believed to be involved in this response to vascular wall injury, and it is likely that interfering with the actions of only one of these factors will prove to be beneficial.

Therefore, therapeutic anti-mitotic agents which reduce or inhibit the abnormal migration and proliferation of smooth muscle cells associated with cardiovascular disorders such as atherosclerosis and vascular hypertrophy associated with hypertension, or resulting from complications following PTCA and causing chronic restenosis are highly desirable.

SUMMARY OF THE INVENTION

In the fast aspect, the present invention provides a new medical use for the hydroxycarbazole compounds of Formula (I), preferably the hydroxylated metabolites of 1-(carbazol-4-yloxy-3-[[2-(o-methoxyphenoxy)ethyl]amino]-2-propanol) (hereinafter referred to as carvedilol), as anti-mitotic agents for inhibition of smooth muscle cell growth.

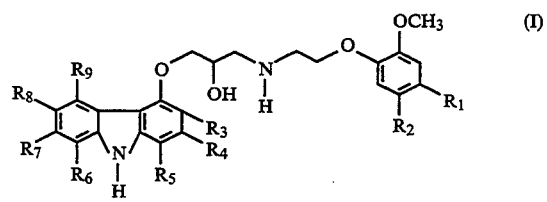

wherein:
$R_1$–$R_9$ are independently —H or —OH, with the proviso that at least one of $R_1$–$R_9$ is —OH.

In a second aspect, the present invention also provides a method of treatment for inhibition of restenosis following PTCA, for suppressing the profession of vascular hypertrophy associated with hypertension, and prevention of the development of atherosclerosis in mammal comprising internally administering to a mammal, preferably a human, in need thereof an effective amount of a compound selected from the consisting essentially of compounds of Formula (I) or pharmaceutically acceptable salts thereof.

DETAILED DESCRIPTION OF THE INVENTION

U.S. Pat. No. 4,503,067 (hereinafter "the '067 patent") discloses carbazolyl-(4)-oxypropanolamine compounds of Formula II:

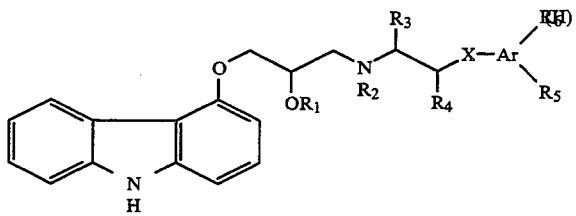

wherein:
- R₁ is hydrogen, lower alkanoyl of up to 6 carbon atoms or aroyl selected from benzoyl and naphthoyl;
- R₂ is hydrogen, lower alkyl of up to 6 carbon atoms or arylalkyl selected from benzyl, phenylethyl and phenylpropyl;
- R₃ is hydrogen or lower alkyl of up to 6 carbon atoms;
- R₄ is hydrogen or lower alkyl of up to 6 carbon atoms, or when X is oxygen, R₄ together with R₅ can represent —CH₂—O—;
- X is a valency bond, —CH₂, oxygen or sulfur;
- Ar is selected from phenyl, naphthyl, indanyl and tetrahydronaphthyl;
- R₅ and R₆ are individually selected from hydrogen, fluorine, chlorine, bromine, hydroxyl, lower alkyl of up to 6 carbon atoms, a —CONH₂ group, lower alkoxy of up to 6 carbon atoms, benzyloxy, lower alkylthio of up to 6 carbon atoms, lower alkylsulphinyl of up to 6 carbon atoms and lower alkylsulphonyl of up to 6 carbon atoms; or
- R₅ and R₆ together represent methylenedioxy;

and pharmaceutically acceptable salts thereof.

This patent further discloses a compound of Formula II better known as carvedilol (1-(carbazol-4-yloxy-3-[[2-(o-methoxyphenoxy)ethyl]amino]-2-propanol), having the structure shown in Formula III:

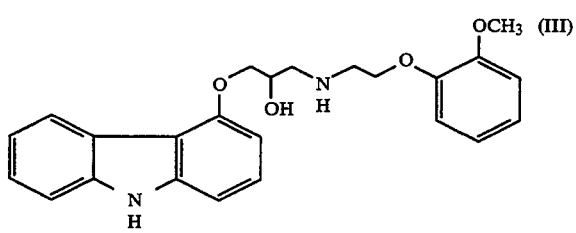

The compounds of the '067 patent, of which carvedilol is exemplary, are novel multiple action drugs useful in the treatment of mild to moderate hypertension and having utility in angina and congestive heart failure (CHF). Carvedilol is known to be both a competitive β-adrenoceptor antagonist and a vasodilator, and is also a calcium channel antagonist at higher concentrations. The vasodilatory actions of carvedilol result primarily from α₁-adrenoceptor blockade, whereas the β-adrenoceptor blocking activity of the drug prevents reflex tachycardia when used in the treatment of hypertension. These multiple actions of carvedilol are responsible for the antihypertensive efficacy of the drug in animals, particularly in humans, as well as for utility in the treatment of angina and CHF. See Willette, R. N., Sauermelch, C. F. & Ruffolo, R. R., Jr. (1990) *Eur. J. Pharmacol.*, 176, 237–240; Nichols, A. J., Gellai, M. & Ruffolo, R. R., Jr. (1991) *Fundam. Clin. Pharmacol.*, 5, 25–38; Ruffolo, R. R., Jr., Gellai, M., Hieble, J. P., Willette, R. N. & Nichols, A. J. (1990) *Eur. J. Clin. Pharmacol.*, 38, S82–S88; Ruffolo, R. R., Jr., Boyle, D. A., Venuti, R. P. & Lukas, M. A. (1991) *Drugs of Today*, 27, 465–492; and Yue, T.-L., Cheng, H., Lysko, P. G., McKenna, P. J., Feuerstein, R., Gu, J., Lysko, K. A., Davis, L. L. & Feuerstein, G. (1992) *J. Pharmacol. Exp. Ther.*, 263, 92–98.

The antihypertensive action of carvedilol is mediated primarily by decreasing total peripheral vascular resistance without causing the concomitant reflex changes in heart rate commonly associated with other antihypertensive agents. Willette, R. N., et al. supra; Nichols, A. J., et al. supra; Ruffolo, R. R., Jr., Gellai, M., Hieble, J. P., Willette, R. N. & Nichols, A. J. (1990) *Eur. J. Clin. Pharmacol.*, 38, S82–S88. Carvedilol also markedly reduces infarct size in rat, canine and porcine models of acute myocardial infarction, Ruffolo, R. R., Jr., et at., *Drugs of Today*, supra, possibly as a consequence of its antioxidant action in attenuating oxygen free radical-initiated lipid peroxidation. Yue, T. L., et at. supra.

Carbazolyl-(4)-oxypropanolamine compounds, in particular carvedilol, have also been disclosed as inhibiting of smooth muscle migration and proliferation in copending patent application Ser. No. 08/026892.

Recently, it has been discovered that the hydroxycarbazole compounds of Formula (I), preferably wherein R₁, R₂, R₃, R₅, R₆ or R₈ are independently OH, are also able to block mitogen-stimulated proliferation of cultured rat aortic vascular smooth muscle cells in vitro. These compounds are potent inhibitors both of migration, measured by PDGF, and proliferation, measured by ³H-thymidine. Because said compounds inhibit the proliferative actions of multiple mitogenic stimuli, the use of said compounds, preferably those compounds wherein R₁, R₂, R₃, R₅, R₆ or R₈ are independently OH, to inhibit the migration and proliferation of smooth muscle cells, and therefore to prevent the therapeutically undesirable sequelae of such proliferation, has a clear advantage over specific growth factor antagonists.

It has been further discovered that the compounds of Formula (I), preferably those compounds wherein R₁, R₂, R₃, R₅, R₆ or R₈ are independently OH, demonstrate superior protective effects against vascular smooth muscle migration and proliferation in blood vessels. More particularly, the compounds of Formula (I) produce potent inhibition of vascular smooth muscle cell proliferation, migration, and neointimal proliferation in arteries subjected to acute injury induced by balloon angioplasty.

To that end, the present invention provides a use for a compound selected from the group consisting essentially of the compounds of Formula (I), preferably those compounds wherein R₁, R₂, R₃, R₅, R₆ or R₈ are independently OH, or a pharmaceutically acceptable salt thereof, said use being for inhibition of proliferation and migration of smooth muscle cells in mammals, preferably human beings, particularly for inhibiting restenosis by angioplasty-induced neointimal proliferation in blood vessels of patients surviving PTCA; for inhibition of development of atherosclerosis; or for suppressing the profession of vascular hypertrophy associated with hypertension.

The present invention also provides a method of treatment for inhibition of proliferation and migration of smooth muscle cells in mammals, preferably human beings, particularly a method of treatment for preventing restenosis by angioplasty-induced neointimal proliferation in blood vessels of patients surviving PTCA; for inhibition of development of atherosclerosis; or for suppressing the progression of vascular hypertrophy associated with hypertension, said method comprising internally administering to a patient in need thereof an effective dose of a pharmaceutical composition comprising a compound of Formula (I), preferably those compounds wherein $R_1$, $R_2$, $R_3$, $R_5$, $R_6$ or $R_8$ are independently OH, or a pharmaceutically acceptable salt thereof.

As further illustrated in the Examples below, compounds of Formula (I) significantly inhibit vascular smooth muscle cell migration in vitro, and inhibit human vascular smooth muscle mitogenesis mediated by a wide variety of different mitogens.

Chemotactic migration of medial smooth muscle cells into the intima is an important first step in the pathogenesis of neointima formation following balloon angioplasty. PDGF is believed to be a key substance for promoting smooth muscle cell migration and proliferation. Ferns, G. A. A., et al., supra; Ross, R. (1986) N. Engl. J. Med. 314 488–500. According to the present invention, compounds of Formula (I) inhibit smooth muscle cell migration induced by PDGF with $IC_{50}$ values ranging from 0.2 to 1.7 $\mu M$. Without being limited by any mechanistic explanation or theory of operation, the ability of these compounds to inhibit myointimal formation in vivo may in part be related to direct inhibition of the physical migration of vascular smooth muscle from the tunic a media into the tunic a intima, and also in part through antioxidant activity of these compounds which may inhibit the recruitment of macrophages and monocytes to the injury site.

While the precise molecular events leading to the anti-proliferative and anti-migratory actions of compounds of Formula (I) await further elucidation, the new medical use of these hydroxylated metabolites of carvedilol and method of treatment using these hydroxylated metabolites of carvedilol according to the present invention afford pronounced protection in an animal model of neointimal formation and stenosis following angioplasty.

Compounds of Formula (I) may be conveniently prepared as described by way of example in Example 1.

Pharmaceutical compositions of the compounds of Formula (I) may be administered to patients according to the present invention in any medically acceptable manner, preferably parenterally. For parenteral administration, the pharmaceutical composition will be in the form of a sterile injectable liquid stored in a suitable container such as an ampule, or in the form of an aqueous or nonaqueous liquid suspension. The nature and composition of the pharmaceutical carrier, diluent or excipient will, of course, depend on the intended route of administration, for example whether by intravenous or intramuscular injection Pharmaceutical compositions of the compounds of Formula (I) for use according to the present invention may be formulated as solutions or lyophilized powders for parenteral administration. Powders may be reconstituted by addition of a suitable diluent or other pharmaceutically acceptable carder prior to use. The liquid formulation is generally a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as ethanol, polyvinyl-pyrrolidone, gelatin, hydroxy cellulose, acacia, polyethylene glycol, mannitol, sodium chloride or sodium citrate.

Alternatively, these compounds may be encapsulated, tableted or prepared in a emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, ethanol, and water. Solid carriers include starch, lactose, calcium sulfate dihydrate, terra alba, magnesium stearate or stearic acid, talc, pectin, acacia, agar or gelatin. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

Dosing in humans for the treatment of disease according to the present invention should not exceed about 100 mg/day of the compounds of Formula I. For prevention of reocclusion following PTCA, the preferred range of dosing is administration of from about 12.5 mg/day to about 100 mg/day of a compound of Formula I in a single dose or multiple doses up to three times dally before, during, and for up to six months post-angioplasty; most preferably the dosage is about 25 mg/day 3 times daily. It will be appreciated that the actual preferred dosages of the compounds being used in the compositions of this invention will vary according to the particular composition formulated, the mode of administration, the particular site of administration, the host being treated, and the particular disease being treated.

No unacceptable toxicological effects are expected when the compounds of Formula I are used according to the present invention.

In the following Examples, all temperatures are in degrees Centigrade (°C.). Unless otherwise indicated, all of the starting materials were obtained from commercial sources. Without further elaboration, it is believed that one skilled in the art can, using the preceding description, utilize the invention to its fullest extent. These Examples are given to illustrate the invention, not to limit its scope. Reference is made to the claims for what is reserved to the inventors hereunder.

EXAMPLES

Example 1

The compound of Formula (I) wherein $R_3$ is —OH and $R_{1-R2}$ and $R_4$–$R_9$ are all H was synthesized as follows and is exemplary of the synthetic route to the compounds of Formula (I).

3-Benzyl-4-hydroxycarbazole

Benzoyl peroxide (881 mg, 2.73 mmol) was added in one portion to a suspension of 4-hydroxycarbazole (500 mg, 2.73 mmol) in 20 ml $CHCl_{13}$ at 25° C. The mixture was stirred for 2 h, then washed with water. The organic layer was dried over sodium sulfate and concentrated. Flash chromatography of the residue (silica, methylene chloride) provided 15 mg of 3-benzyloxy-4-hydroxycarbazole. MS i3 ($DCI/NH_3$): 304.2 $(M+H)^+$.

Subsequent steps to yield the product are well-known: reaction with epichlorohydrin, then 2-methoxyphenylethylamine, and finally saponification of the benzoyl ester.

Example 2

Migration of Vascular Smooth Muscle

The procedure for assessing vascular smooth muscle cell migration was described previously in Hidaka, Y., Eda, T., Yonemoto, M. & Kamei, T. (1992) *Atheroscler.* 95, 87–94. Briefly, rat aortic vascular smooth muscle cells (passage 3) were suspended ($1 \times 10^6$ cells/ml) in serum free DMEM supplemented with 0.2% (w/v) bovine serum albumin (Sigma). Migration assays were performed in modified Boyden chambers using Transwell (Costar, Cambridge, Mass.) cell culture chambers with a polycarbonate 8µm pore size membrane. PDGF was dissolved in DMEM and placed in the lower compartment in the presence, or absence, of compounds of Formula (I) wherein $R_1$, $R_2$, $R_3$, $R_5$, $R_6$ or $R_8$ are independently OH. Vascular smooth muscle cells ($5 \times 10^5$) were then loaded in the upper compartment and incubated for 24 h at 37° C. in a humidified atmosphere containing 5% $CO_2$. Non-migrated cells on the upper surface were scraped away gently and washed three times with PBS. Filters were fixed in methanol and stained with Giemsa. The number of vascular smooth muscle cells per 100×high power field (HPF) that had migrated to the lower surface of the filters was determined microscopically. Four HPFs were counted per filter. Experiments were performed either in duplicate or triplicate.

PDGF produced concentration-dependent increases in the migration of rat vascular smooth muscle cells with maximal effect obtained at a concentration of 1 nM. When compounds of Formula (I) wherein are independently $R_1$, $R_2$, $R_3$, $R_5$, $R_6$ or $R_8$ is OH were placed in the lower chamber with PDGF, the migration response was inhibited significantly in a concentration-dependent manner. $IC_{50}$ values for compounds of Formula (I) wherein $R_1$, $R_2$, $R_3$, $R_5$, $R_6$ or $R_8$ are independently OH were as follows.

| Position of OH group | $IC_{50}$ [µM] |
| --- | --- |
| $R_1$ | 0.99 |
| $R_2$ | 0.41 |
| $R_3$ | 0.20 |
| $R_5$ | 0.18 |
| $R_6$ | 1.72 |
| $R_8$ | 0.36 |

The above description fully discloses how to make and use the present invention. However, the present invention is not limited to the particular embodiment described hereinabove, but includes all modifications thereof within the scope of the claims.

What is claimed is:

1. A method of treatment for inhibition of proliferation and migration of smooth muscle cells in mammals comprising internally administering to a mammal in need thereof an effective amount of a compound of Formula (I):

wherein:

$R_1$–$R_9$ are independently —H or —OH, with the proviso that at least one of $R_1$–$R_9$ is OH, or a pharmaceutically acceptable salt thereof.

2. A method of treatment according to claim 1 wherein said mammal is human.

3. A method of treatment according to claim 1 wherein in said compound of Formula (I), $R_1$ is OH and $R_2$–$R_9$ are H.

4. A method of treatment according to claim 1 wherein in said compound of Formula (I), $R_2$ is OH and $R_1$, and $R_3$–$R_9$ are H.

5. A method of treatment according to claim 1 wherein in said compound of Formula (I), $R_3$ is OH and $R_1$, $R_2$, and $R_4$–$R_9$ are H.

6. A method of treatment according to claim 1 wherein in said compound of Formula (I), $R_5$ is OH and $R_1$–$R_4$ and $R_6$–$R_9$ are H.

7. A method of treatment according to claim 1 wherein in said compound of Formula (I), $R_6$ is OH and $R_1$–$R_5$ and $R_7$–$R_9$ are H.

8. A method of treatment according to claim 1 wherein in said compound of Formula (I), $R_8$ is OH and $R_1$–$R_7$ and $R_9$ are H.

9. A method of treatment according to claim 1 wherein human patients surviving percutaneous transluminal coronary angioplasty (PTCA) are administered an effective dose of a pharmaceutical composition comprising a compound of Formula (I), to inhibit restenosis by angioplasty-induced neointimal proliferation in blood vessels following PTCA.

10. A method of treatment according to claim 9 wherein said pharmaceutical composition is suitable for parenteral administration.

11. A method of treatment according to claim 9 wherein in said compound of Formula (I), $R_1$ is OH and $R_2$–$R_9$ are H.

12. A method of treatment according to claim 9 wherein in said compound of Formula (I), $R_2$ is OH and $R_1$, and $R_3$–$R_9$ are H.

13. A method of treatment according to claim 9 wherein in said compound of Formula (I), $R_3$ is OH and $R_1$, $R_2$, and $R_4$–$R_9$ are H.

14. A method of treatment according to claim 9 wherein in said compound of Formula (I), $R_5$ is OH and $R_1$–$R_4$ and $R_6$–$R_9$ are H.

15. A method of treatment according to claim 9 wherein in said compound of Formula (I), $R_6$ is OH and $R_1$–$R_5$ and $R_7$–$R_9$ are H.

16. A method of treatment according to claim 9 wherein in said compound of Formula (I), $R_8$ is OH and $R_1$–$R_7$ and $R_9$ are H.

17. A method of treatment according to claim 1 wherein human patients are administered an effective dose of a pharmaceutical comprising a compound of Formula (I) for inhibition of development of atherosclerosis.

18. A method of treatment according to claim 17 wherein said pharmaceutical composition is suitable for parenteral administration.

19. A method of treatment according to claim 17 wherein in said compound of Formula (I), $R_1$ is OH and $R_2$–$R_9$ are H.

20. A method of treatment according to claim 17 wherein in said compound of Formula (I), $R_2$ is OH and $R_1$, and $R_3$–$R_9$ are H.

21. A method of treatment according to claim 17 wherein in said compound of Formula (I), $R_3$ is OH and $R_1$, $R_2$, and $R_4$–$R_9$ are H.

22. A method of treatment according to claim 17 wherein in said compound of Formula (I), $R_5$ is OH and $R_1$–$R_4$ and $R_6$–$R_9$ are H.

23. A method of treatment according to claim 17 wherein in said compound of Formula (I), $R_6$ is OH and $R_1$–$R_5$ and $R_7$–$R_9$ are H.

24. A method of treatment according to claim 17 wherein in said compound of Formula (I), $R_8$ is OH and $R_1$–$R_7$ and $R_9$ are H.

25. A method of treatment according to claim 1 wherein human patients are administered an effective dose of a pharmaceutical composition comprising a compound of Formula (I) for suppressing the progression of vascular hypertrophy associated with hypertension.

26. A method of treatment according to claim 25 wherein in said pharmaceutical composition is suitable for parenteral treatment.

27. A method of treatment according to claim 25 wherein in said compound of Formula (I), $R_1$ is OH and $R_2$–$R_9$ are H.

28. A method of treatment according to claim 25 wherein in said compound of Formula (I), $R_2$ is OH and $R_1$, and $R_3$–$R_9$ are H.

29. A method of treatment according to claim 25 wherein in said compound of Formula (I), $R_3$ is OH and $R_1$, $R_2$, and $R_4$–$R_9$ are H.

30. A method of treatment according to claim 25 wherein in said compound of Formula (I), $R_5$ is OH and $R_1$–$R_4$ and $R_6$–$R_9$ are H.

31. A method of treatment according to claim 25 wherein in said compound of Formula (I), $R_6$ is OH and $R_1$–$R_5$ and $R_7$–$R_9$ are H.

32. A method of treatment according to claim 25 wherein in said compound of Formula (I), $R_8$ is OH and $R_1$–$R_7$ and $R_9$ are H.

* * * * *